US011642311B2

(12) United States Patent
Mota Leite Machado Mariz et al.

(10) Patent No.: US 11,642,311 B2
(45) Date of Patent: May 9, 2023

(54) NON-INVASIVE OCULAR DRUG DELIVERY INSERT TECHNOLOGY (71) Applicant: UNIVERSIDADE DE COIMBRA, Coimbra (PT)

(72) Inventors: Marcos João Mota Leite Machado Mariz, Coimbra (PT); Paula Cristina Nunes Ferreira Calvinho, Condeixa-a-Nova (PT); Maria Helena Mendes Gil, Coimbra (PT); Joaquim Carlos Neto Murta, Coimbra (PT)

(73) Assignee: UNIVERSIDADE DE COIMBRA, Coimbra (PT)

( * ) Notice: Subject to any disclaimer, the term of this patent is extended or adjusted under 35 U.S.C. 154(b) by 6 days.

(21) Appl. No.: 16/077,493

(22) PCT Filed: Feb. 10, 2017

(86) PCT No.: PCT/IB2017/050731
§ 371 (c)(1),
(2) Date: Aug. 13, 2018

(87) PCT Pub. No.: WO2017/137934
PCT Pub. Date: Aug. 17, 2017

(65) Prior Publication Data
US 2019/0046434 A1 Feb. 14, 2019

(30) Foreign Application Priority Data
Feb. 12, 2016 (PT) .......................... 109154

(51) Int. Cl.
*A61K 9/00* (2006.01)
*A61K 47/34* (2017.01)
*A61K 31/192* (2006.01)
*A61K 31/4709* (2006.01)
*A61K 45/06* (2006.01)
*B29D 11/02* (2006.01)
*A61K 31/165* (2006.01)
*B29D 11/00* (2006.01)
*B29K 67/00* (2006.01)
*B29K 71/00* (2006.01)
*B29K 105/00* (2006.01)

(52) U.S. Cl.
CPC .......... *A61K 9/0051* (2013.01); *A61K 31/165* (2013.01); *A61K 31/192* (2013.01); *A61K 31/4709* (2013.01); *A61K 45/06* (2013.01); *A61K 47/34* (2013.01); *B29D 11/023* (2013.01); *B29D 11/00096* (2013.01); *B29K 2067/046* (2013.01); *B29K 2071/02* (2013.01); *B29K 2105/0035* (2013.01); *B29K 2105/0085* (2013.01)

(58) Field of Classification Search
CPC ..... A61K 9/0051; A61K 2300/00; A61K 9/20
See application file for complete search history.

(56) References Cited

U.S. PATENT DOCUMENTS

| | | | | | |
|---|---|---|---|---|---|
| 3,993,071 | A | * | 11/1976 | Higuchi | A61K 9/0051 424/428 |
| 5,137,728 | A | * | 8/1992 | Bawa | A61F 9/0017 424/422 |
| 6,331,313 | B1 | * | 12/2001 | Wong | A61K 9/0051 424/427 |
| 2005/0256528 | A1 | * | 11/2005 | Beavers | A61F 2/1675 606/107 |
| 2006/0024350 | A1 | * | 2/2006 | Varner | A61L 31/06 424/427 |
| 2007/0053990 | A1 | * | 3/2007 | Persyn | A61K 9/5089 424/490 |
| 2009/0175938 | A1 | * | 7/2009 | Cifter | A61K 9/209 514/33 |

(Continued)

OTHER PUBLICATIONS

Thote et al., Reduction in the Initial-Burst Release by Surface Crosslinking of PLGA Microparticles Containing Hydrophilic or Hydrophobic Drugs, Drug Dev Ind Pharm, Jan. 2005;31(1):43-57, printed from https://pubmed.ncbi.nlm.nih.gov/15704857/, 1 page, Abstract only.*
Peng et al (Medical Hypothesis, Discovery and Innovation Ophthalmology Journal, 2014, vol. 3, pp. 3-8) (Year: 2014).*
J . E . Mealy et al: I n vi t ro characterization of a controlled-release ocular insert for delivery of brimonidine ta rt rate, Acta Biomaterialia, vol. 10, No. I,Sep. 28, 2013 (Sep. 28, 2013), pp. 87-93, XP055377989, Amsterdam, NL ISSN: 1742-7061, DOI: 10.1016/j.actbio.2013.09. 024.

(Continued)

*Primary Examiner* — Mark V Stevens
(74) *Attorney, Agent, or Firm* — Mark M. Friedman (57) ABSTRACT

Non-invasive Ocular Drug Delivery Insert Technology. The invention concerns an ocular insert which is a new biocompatible polymer-based controlled drug delivery system (CDDS) applicable to a variety of drugs and other compounds for the treatment of different ocular pathologies. This ocular insert allows releasing of at least one drug under suitable concentration levels during suitable periods of time. The device may be inserted in the lower or upper fornix conjunctiva, in a non-invasive way, meaning that the patient will be able to place the device himself, without intervention of medical specialized staff. The insert of the invention will release the drug in such a controlled rate that will allow the drug release up to 300 days by either a "Fickian" or a linear profile according to the intend purpose or pathology. The insert can be prepared with different shapes (spherical or spherical dome) and/or architectures (monolithic/layered either with or without a drug core) allowing the incorporation of at least one drug which can be released at different rates. The size, shape and design of the insert is adjusted in order to tune the drug(s) delivery profile(s) and to inhibit the risk of displacement or expulsion.

11 Claims, 4 Drawing Sheets

(56) References Cited

U.S. PATENT DOCUMENTS

2010/0311808 A1   12/2010  Lyons
2012/0021518 A1    1/2012  Hart et al.
2012/0059338 A1    3/2012  Beeley

OTHER PUBLICATIONS

Ng Xu Wen et al: 11A biodegradable ocular implant for long-term suppression of intraocular pressure ,Drug Delivery and Translational Research, Springer, Germany, vol. 5, No. 5, Jun. 23, 2015 (Jun. 23, 2015), pp. 469-479, XP035530672, ISSN: 2190-393X, DOI: 10.1007/SI3346-015-0240-4.

* cited by examiner

NON-INVASIVE OCULAR DRUG DELIVERY INSERT TECHNOLOGY

FIELD OF THE INVENTION

The present invention is related to a biocompatible ocular insert with polymeric composition, designed for "in vivo" sustained drug release to be applied in the treatment of different ocular pathologies.

BACKGROUND OF THE INVENTION

In the area of ophthalmology, the conventional method of drops topical application involves repeated administrations of the drugs solutions and the drugs concentration profiles are characterized by extreme fluctuations with an excessive concentration stage, followed by a brief period of correct dose and ending in a long underdosing period. Moreover, it is necessary to take into consideration the drainage of the lacrimal film and the small corneal permeability which require the use of high doses of drug in order to secure the intraocular therapeutic level. Since only 1 to 3% of the drug penetrates the cornea [1, 2] and the remainder is absorbed by systemic routes, high concentrations can bring toxic side effects at a systemic level. To overcome these obstacles, many polymers have been implemented both in ophthalmic preparations and in solid drug delivery systems.

Preparation of systems that release drug in a predictable and reproducible at a specific location and for a long period of time has much merit, since drug delivery is dependent on many factors, including the concentration and physicochemical properties of the drug, the time of contact with the biological system, the mechanical, physical, chemical, and biochemical features of the drug carrier. Ideally a drug delivery system provides the drug only when and where it is needed and within the appropriate concentration for the desired therapeutic effect. Therefore, it is desirable to control the release of the pharmacological agent to maintain the drug concentration above the minimal effective concentration (MEC) and below the minimal toxic concentration (MTC). This concentration interval is known as the therapeutic range.

Ocular Controlled Drug Delivery Systems (CDDS) allow therapeutic agents to be available in the eye for extended periods of time at the desired concentrations. Furthermore, the following advantages when compared to conventional eye drop treatment should also be considered:

- Lower systemic toxicity, since lower amounts of drug are used when comparing to the eye drops treatment and also the fact that this form of treatment is targeted to the eye where it stays for longer time;
- Improved patient compliance, namely for treatment of chronic diseases, such as glaucoma, as drug administration frequency is significantly reduced;
- Improved safety, as accurate dosing is achieved;
- Better product stability as drugs are in dried state;
- No need for preservatives that could generate inflammatory reactions.

Solid CDDS can be easily grouped as implants, if a medical procedure such as a surgery or an injection (invasive application) is needed to assure the correct placement of the CDDS, or as inserts, when the dosage form of application is non-invasive and made by the patient himself.

Implants: these CDDS requires a surgery or at least a medical procedure perform by trained personnel, with the associated risks and costs. Furthermore, patients must necessarily have access not only to the device but also to healthcare personnel and premises. This type of CDDS can release the drugs for long periods of time—some studies revealed drug release profiles of almost two years—and some might need to be removed after releasing all the loaded drug.

Inserts: CDDS for ocular used under the form of insert exist since the 1975, when Ocusert® was marketed in the USA. Since then different shapes, designs, polymers and drug immobilization techniques have been used. These devices are placed by the patient in the front section of the eye—in the fornix conjunctiva, behind the lower or upper eyelid, over the sclera or over the corneal surface. However, most of them never reached the market and for those few with an FDA marketing authorization some disadvantages were found—the higher costs when compared to eye drops; accidental expulsion; patient discomfort and difficulty of handling—making them a second-choice of treatment for both patients and physicians. An explored approach, similar to the drug loading of an intraocular lens (IOL), was applied to normal contact lenses. Several studies report that, in addition to the vision correction function, the hydrophilic contact lenses could be pre-soaked in a variety of drug solutions in order to slightly improve the residence time of the drugs—this improvement was however, no higher than two hours.

Ocular Implants

The development of intraocular implants was triggered by the opportunity of delivering the drugs directly to the intended site of action without suffering elimination by the lacrimal fluid drainage system. Furthermore the physical and chemical barrier presented by the cornea to intraocular availability of drugs is overcome.

These CDDS present several advantages when compared to topical eye drop administration. With a controlled delivery rate on the local of action less drug is needed to complete the treatment, which means less side-effects or systemic toxicity as well as decreased costs associated with of treatment.

Depending on the site of action these CDDS can be implanted below the retina, in the vitreous chamber, sclera, capsule, posterior chamber, conjunctiva or lacrimal puncta. For each purpose, different shapes have been developed—rods, plugs, filaments, discs, pellets, etc. The first implants with prolonged and controlled drug release were made of non-biodegradable polymers (like poly(vinyl alcohol), poly (ethylene-co-vinyl acetate) or polysulfone). When these implants were used, a second medical intervention to remove the empty shell was therefore required. With the emergence of new devices composed of long-term soluble polymers like poly(lactic acid)—PLA; poly(glycolic acid)—PGA; polycaprolactone—PCL; polyanhydrides and poly (ortho esters), a second surgery was no longer needed. However, degradation of ocular implants is normally uncontrollable, namely in the last stages of the process, conducting to unpredictable drug release and eventually a final burst is observed. Some techniques and strategies have been described to refine the degradation kinetics and include: different polymer ratios; different molecular weight of the same polymer and tuned crosslinking.

The choice of polymers must thus be based on the drug characteristics and the foreseen duration of its release.

For acute disease treatment (or prevention, as in postoperative periods) the drug release can be faster than the degradation of the dosage form, as only one implantation is necessary. In these cases, diffusion is the main factor affecting the drug release. For the treatment of chronic pathologies, device degradation should follow the drug release to allow further implantation, which implies that polymer solubility is the critical step for drug release.

Ozurdex®

Ozurdex® is a tiny rod shape biodegradable implant (0.45 mm in diameter and 6.5 mm in length) containing 0.7 mg of dexamethasone. It was approved by FDA in 2009 for treatment in adults of macular edema and retinal vein occlusion and in 2010 for uveitis. It was the first biodegradable implant to be injected in the vitreous cavity through a specially designed injector with a 22-gauge needle based on Novadur™, a drug delivery technology. This CDDS is made of poly(lactic-co-glycolic acid) (PLGA).

Intraocular pressure increase, cataracts and vitreous detachment have been reported as side-effects after implantation of this device.

A similar strategy, designed to release brimonidine to prevent apoptosis of photoreceptors is now under clinical tests.

Surodex®

Surodex® is a cylindrical pellet (0.5 mm in diameter and 1.0 mm in length) containing 60 µg of micro dispersed dexamethasone into a PLGA copolymer matrix. Surodex is implanted in the anterior chamber to prevent postoperative inflammation in cataract surgery or corneal graft rejection. Intracameral and intrascleral application may also be considered for treatment of uveitis. Also marketed as Oculex®, this biodegradable device allows sustained dexamethasone release over 7 days. However, a study demonstrated that despite achieving higher intraocular drug levels than conventional 0.1% dexamethasone eye drops, no significant benefits were observed with the use of this technology. Other studies revealed a good control of intraocular pressure for at least 20 months, whereas the total release of corticosteroid from the implant was achieved within 2 weeks after implantation. This device degrades in approximately 2 years without causing any cell damage.

Durasert®

Durasert® is a delivery technology system patented by Bausch & Lomb for development of intraocular CDDS. Basically, a drug core is coated by layers of different polymers and a suture tab made from poly(vinyl acetate) (PVA) is used to anchor the implant to the "pars plana" through a suture hole. The Vitrasert® was the first implant based on Durasert® design approved by FDA. It is a non-erodible polymer-based sustained release delivery system containing 4.5 mg of ganciclovir compressed into a 2.5 mm diameter by 1 mm thick tablet. The tablet is entirely coated with PVA and with a discontinuous film of ethylene vinyl acetate (EVA). The drug diffuses through the semipermeable PVA layer but when it reaches the EVA layer the release is then controlled by the discontinuity of this impermeable layer.

This CDDS is used for the local treatment of cytomegalovirus (CMV) retinitis, namely in patients with acquired immunodeficiency syndrome, releasing the antiviral agent for at least 3 months at a sustained rate. Clinical studies demonstrated that CMV retinitis progression is halted for 6 up to 8 months (average).

Additionally to the commonly observed complication associated to intraocular implants, (that may include injury to the eye; infection; movement or ejection of the implant; and wound complications following the surgery) there is an increased risk of extraocular CMV infection.

Using the same Durasert® structure, Bausch & Lomb created Retisert® for delivery of a synthetic corticosteroid, fluocinolone acetonide to the posterior segment of the eye. This system was approved by FDA for the treatment of non-infectious posterior uveitis. In this implant, 0.59 mg of the drug is compressed in a 1.5 mm diameter tablet which is then encased in a silicone elastomer cup containing a release orifice. A PVA layer near the orifice works as a diffusional barrier for the drug being solubilized by the water entering the cup. By varying the size of the release pore and the permeability of the PVA layer, CDDS with different release rates can be obtained.

Starting with a release rate of 0.6 µg/day, it decreases to 0.3-0.4 µg/day during the first month, and keeps this rate during approximately 30 months.

Both Vitrasert® and Retisert® must be removed after depletion of the drugs from the devices.

Punctal Plug

Punctal plugs were initially developed to occlude the lacrimal puncta in order to increase the residence time of drugs administered by eye drops They were initially made of collagen (temporary), PCL (extended duration) or silicone (permanent). However, studies conducted with antiglaucoma agents did not revealed any significant clinical benefits from blocking the drainage of the lacrimal film with this device. Later on, two companies developed punctual plugs containing different prostaglandins (anti-glaucoma drugs) with various doses and release rates. However, besides the prolonged residence time, no significant intraocular pressure reduction was observed. Despite the clinical failure of these initial tests, these devices have the advantage of being easily implanted and explanted, which reduces costs and avoids complications in the posterior segment of the eye associated to intraocular implants. The major drawback for the use of ocular implants is the need for a surgical implantation, involving costs and associated risks that make this treatment strategy difficult to accept by both patient and physician. The most commonly observed complications for posterior segment of the eye implantation are inflammation, vitreous hemorrhage, cataract, retinal detachment, endophthalmitis, cystoid macular edema and the formation of tenacious epiretinal membranes [3].

Punctal plug, subconjunctival or episcleral implants have reduce these adverse effects and the implantation can be made with local anaesthesia, improving patient compliance.

Ocular Inserts

Ocular inserts are defined as preparations with a solid or semisolid consistency, whose size and shape are especially designed for ophthalmic application. These inserts are placed in the lower fornix conjunctiva and, less frequently, in the upper fornix conjunctiva or on the cornea. They are usually composed of a polymeric vehicle containing the drug and are mainly used for topical therapy.

Since the physicochemical properties and functional groups vary from drug to drug, and the desired concentration of each, it is not possible to obtain a universally applicable polymer, suitable for all drug-based ophthalmologic therapies. Therefore, the knowledge of the properties of polymers and the creation of methods to change these properties is essential for the development of ocular inserts.

Based on the nature of the polymer used, these systems can be classified as soluble or insoluble. The obvious advantage of soluble systems is that it is not necessary to be removed after the functional period. Furthermore, the degradation of the soluble systems makes it more comfortable for the patient than insoluble ones, unless degradation products cause inflammatory reactions. However, the speed of degradation, whether hydrolytic or enzymatic, varies depending on the rate of production and removal of the tear fluid or on the concentration of enzymes, which are different for every patient. Consequently, the soluble systems are more susceptible to variations in the kinetics of drug release than the insoluble ones. In insoluble systems, release kinetics depends mainly on the interactions between the polymer and the drug rather than in physiological conditions of the eye, thus kinetics can easily be changed by manipulating those interactions. Another advantage of insoluble inserts is the fact that expulsion is always the reason for the disappearing of the CDDS. On the other hand, degradation variability of soluble CDDS that is observed from patient to patient, does not allow concluding whether expulsion or rapid degradation as being the cause for the disappearance of the dosage form. Finally, the placement of any of these CDDS (soluble or insoluble) in the eye does not require surgery, so their removal is easy in either case.

Soluble systems are usually monolithic constructs with drug dispersed or dissolved throughout the entire matrix. Two main mechanisms are responsible for the CDDS disintegration solubilisation (after polymer swelling) and erosion (corresponding to a hydrolytic process). In contrast, the insoluble systems can be made of several polymeric layers, consequently showing a wide range of release profiles.

In conclusion, during synthesis of an ocular insert pros and cons of disintegration must be weighed, bearing in mind possible interactions with the immobilized drug.

Insoluble CDDS

Contact Lenses

Various soft contact lenses (hydrophilic) have been used as ocular inserts in addition to its function of correcting vision. Immobilization is achieved by placing the lens in a solution containing the drug—pre-soaked lenses. Glaucoma drugs and antibiotics have been the most widely used in this approach. When the lenses are placed in the eye, the release occurs at a slower rate compared to the corresponding aqueous solution. However, the entire amount of the drug is released in less than 30 minutes [4]. In addition to a short period of release, the need to soak the lens in the solution containing the drug, results in loss of sterility of the lens and the absorption of contaminants present in the solution. The use of contact lenses soaked in solutions of drugs is thus limited to certain cases where the advantage of choosing the drug and its concentration in the lens overlap the short release period. Alternatively, the drug may be immobilized in the lens by adding the drug to the solution of monomers. The polymerization is then done in the presence of the drug. This method can only be applied if the drug does not affect the polymerization reaction and the final properties of the lens, especially their optical properties. Under these conditions the release rate is slower, reaching up to 180 hours [5, 6, 7]. Alvarez-Lorenzo et al. [8] tested with success the molecular imprinting technology to increase the load of norfloxacin and the release time in soft acrylate contact lenses. These authors used acrylic acid as a functional monomer (template molecule) to form functional imprinted cavities and performed the polymerization in the presence of the drug, thus, making the monomers to arrange themselves around the drug molecules according to their interaction capability. The polymerization maintains the matrix structure and after the removal of the template molecules, recognition cavities complementary in shape and functionality (i.e. specific receptors) to the drug are obtained.

Supercritical solvent impregnation (SSI) technology was successfully used to load contact lenses with two antiglaucoma drugs [9]. Using ethanol or water as impregnation cosolvents, the oxygen permeability and the thermo-mechanical properties of the contact lenses were kept. SSI technique is an excellent loading strategy when the polymerization reaction is known to cause the degradation of drugs (e.g. due to high temperatures or acidic conditions).

Some authors immobilized silicone particles, loaded with different drugs, during the polymerization reaction of soft contact lenses composed of hydroxyethyl methacrylate, to reduce the abrupt initial release (generally called the burst effect) and to prolong the drug residence time in the eye [10, 11].

The main drawback of this drug release strategy is its reduced applicability since it is only suitable for patients who need vision correction. Also, the continuation of the treatment requires the removal and eventually the substitution of the contact lens after complete release of the drug.

Ocusert®

The Ocusert® is a pilocarpine delivery system made for chronic treatment of glaucoma. It consists of three layers—two external composed of ethyl acetate and an internal with pilocarpine immobilized in alginate [12].

Around the inner layer there is a ring with ethyl acetate impregnated with titanium dioxide to allow visualizing the systems during its placement. The release rate is controlled by polymer composition, the thickness of the outer layers, by the solubility of pilocarpine and the presence of additives. The kinetics of release of pilocarpine is due in part to the solubility of the drug—that presents amphoteric characteristics, being soluble in both the hydrophobic outer layers and in the aqueous tear fluid. The water is kept out of the delivery system by the hydrophobic membranes.

The Ocusert® has two formulations on the market—Pilo-20 and Pilo-40, with release rates of 20 and 40 μg/hour respectively, for the period of one week. The higher rate of Pilo-40 is achieved by decreasing the thickness of the outer membranes that control the release and adding a plasticizer, diethylhexyl phthalate, to those membranes. Studies by several researchers [13, 14, 15] demonstrated that this system has a good clinical efficacy and does not cause disturbances in vision. However, its use for the delivery of other drugs requires significant modifications in the polymers, with a consequent reduction of the control of diffusion membranes. Other problems include the high cost, difficulty in handling, accidental expulsion and foreign body sensation.

Ocufit®

The Ocufit® is a tetracycline-loaded rod shaped device made of silicone elastomer, designed to fit the shape and size of the human fornix conjunctiva—1.9 mm in diameter and 25-30 mm in length. Katz and Blackman [16] reported that cylindrical shape inserts were better tolerated and expulsion significantly less frequent than that of oval, flat inserts. When placed in the upper fornix conjunctiva, devices were retained for 2 weeks or more in 70% of the cases, releasing 45% of the drug with an initial burst in the first day followed by a constant rate over the remaining period of time. Moreover, active disease (e.g. bacterial, allergic and adenoviral conjunctivitis, trachoma, episcleritis, anterior uveitis, corneal ulcers or scars) did not overtly affect the ability of the patients to retain the inserts.

Mydriasert®

Mydriasert® is a retro palpebral insoluble-matrix system containing phenylephrine and tropicamide and a potential alternative to eye drops to induce mydriasis prior to cataract surgery. It's a white to yellowish-white, oblong shaped (4.3 mm×2.3 mm) tablet and its composition is based on a combination of ammonio methacrylate copolymer, polyacrylate and ethyl cellulose. It should be placed 2 hours before the surgery. When kept for more than 2 hours, local adverse reactions were observed—stinging, blurred vision and visual discomfort.

Minidisc

This CDDS is not yet in the market but the way that shape, size and design were always taken in consideration in its conception, makes Minidisc a very interesting system. Throughout its development, shape and size were considered essential criteria for obtaining a good, comfortable ocular insert, with the highest acceptance from the patient. After many tests, the optimal design was achieved based on the shape of the contact lens but with smaller dimensions. This shape allows to easily placing the insert behind the lid without affecting vision, oxygen permeability and comfort of the patient. The minidisc can be placed anywhere in the lid and because of its circular shape there is no need to align it according to an axis as with Lacrisert® (cylinder) and SODI (oval disc). The anterior and posterior curvatures were optimized after clinical trials using minidiscs without drug, to improve comfort and reduce the movement of the system within the eyelid. In addition to the anatomical features, the development of Minidisc® was based on ocular physiology and pharmacokinetics of different drugs, yielding systems composed of different polymers with tailored properties for the different drugs: crosslinked methacrylate polymers were synthesized to delivery hydrophobic drugs while Bawa et al. [17] used flexible dimethylsiloxane minidiscs for entrapment of hydrophilic drugs. Despite the insoluble nature of the initial minidiscs, the same design has already been tested with the biodegradable polymer hydroxypropyl cellulose and results showed that the placement in the eye was substantially easier than with the Lacriset®, despite being also prepared from the same biodegradable polymer.

Notwithstanding the advantages of its geometry, the polymer/drug interaction (solubility, non-covalent linking, etc.) and the resulting release kinetics will always dictate the success of any new Minidisc®.

Soluble DDS

Lacrisert®

It is a drug delivery system used in the treatment of dry eye syndrome. It has the shape of a small cylinder (3.5 mm long) and is composed of hydroxypropyl cellulose. Although initial studies [18, 19] indicate advantages of Lacrisert® over artificial tears, later studies [20] show that it use can cause vision blur, eye irritation and even bond the eyelids together. The verified irritation may partly be due to the placement procedure, which is quite complicated and difficult especially if performed by the patient. For these reasons, this system is only used in situations where the treatment with artificial tears is not sufficient.

SODI

The SODI (Soluble Ocular Drug Insert) is a small oval ocular insert whose composition consists essentially of poly(acrylamide) containing the drug. The rate of drug release can be altered form 12 up to 24 hours using ethyl acrylate and vinyl pyrrolidone as comonomers. This system has been applied to release pilocarpine and several antibiotics, having demonstrated clear advantages over the conventional administration system by ophthalmic drops.

Collagen Corneal Shields

Initially developed by Fyodorov (a scientist from the former USSR) [21] are marketed by an American company as Biocor-12, Biocor-24 and Biocor-72, depending on the collagen dissolution time (in hours) and not the time release of the drug. These ocular inserts, composed of pig sclera collagen, are 14.5 mm in diameter and 0.1 mm thick. The different rates of dissolution are achieved by crosslinking the collagen with ultra-violet light. As the pre-soaked contact lenses, these shields are placed in a solution containing the drug to absorb and retain it. Consequently, the drug is rapidly released (within hours), with a much higher rate than the one of collagen's dissolution. Later on, some research groups incorporated gentamicin during the preparation of a collagen shield [22, 23, 24] but unlike what was verified with the contact lenses, the practical effects of this incorporation were minimal.

It has been reported that collagen shields can cause discomfort and reduced visual acuity. Collagen degradation can also induce immune response and inflammation [25]. Given the variation degradation from patient to patient, collagen shields have a greater variation in the release kinetics than the contact lenses. In addition to its function as a drug delivery system, it was shown that the collagen shields promote healing of the cornea and lubricate the eyeball [26].

Worldwide, pharmaceutical companies (new-born ones and market leaders), research groups and ophthalmologist are cooperating to improve ocular drug release—either by synthesizing news polymers, inventing new designs or discovering more efficient sites to insert the ocular CDDS.

In recent years many researchers have focused on the development of new ocular inserts, some patenting their work [27, 28] other developing comparative studies with different polymers [29, 30]. U.S. Pat. No. 4,438,123 [27] describes the preparation of ophthalmic compositions containing carbonic anhydrase inhibitors for topical application in the treatment of elevated intraocular pressure, while European Patent 1972344A1 [28] refers to an eye drop formulation for the prevention and treatment of several ocular conditions. Despite the fact that, in both cases the inventors claim the possibility of drug administration by using an ophthalmic insert, no experimental results that support the hypothesis of using an insert to achieve suitable drug delivery profiles are provided in either case, unlike the herein embodied invention. Also, the simultaneous release of more than one drug under similar or distinct profiles is not addressed in either of these patents.

The research in the area of the development of new ophthalmic inserts is still under the focus of several authors, and recently other publications have reported the preparation of devices designed to be applied in the treatment of some ophthalmic diseases. Gevariya et al [31] published a work reporting the preparation of inserts based on different mixtures of polyethylene oxide, hydroxypropyl cellulose and ethyl cellulose. These systems contained levofloxacin and "in vitro" studies showed that the drug release profile was sustained for the maximum period of 24 h and that the prepared inserts were suitable to be used as one-day inserts. Khurana et al [32] reported the preparation and evaluation of an ocular insert for the sustained delivery of gatifloxacin sesquihydrate. The insert measured 5.5 mm and was composed of sodium alginate, polyvinyl alcohol and glycerine, crosslinked with calcium chloride. The results obtained by the researchers showed that this system was able to deliver the drug in a sustained way until a maximum period of 11 h. Other authors, like Jethava and co-workers [33] have developed a device containing ketorolac tromethamine (a nonsteroidal anti-inflammatory drug) designed for the treatment of seasonal allergic conjunctivitis. This device was a bioadhesive "in situ" gelling ocular insert and all the formulations tested by these authors presented approximately 90-95% of drug release at the end of 12 h. These results indicate that none of the prepared systems was suitable to incorporate drugs for longer treatments like the ones required by chronic diseases and experimentally achieved and demonstrated by the ocular insert embodying the invention. In 2016, de Souza and collaborators [34] developed new inserts prepared from chitosan and containing brimonidine tartrate. These systems showed to be biocompatible and provided controlled release of the incorporated drug for a 30 days period. However, the authors were not able to extend drug release to longer periods of time or to obtain different release profiles by changing the insert architecture and/or shape, unlike the ocular insert embodying the invention.

Briefly, it is clear that, despite the reported research in the area of development of ocular inserts, the drug release profiles obtained so far are short and not suitable for chronic diseases such as glaucoma. Many polymers have been used—silicones, poly(acrylate), poly(methacrylate), poly (vinyl acetate), celluloses, polyols, polypeptides, chitin, etc.—to immobilize many drugs—anti-glaucoma, anti-inflammatory, antibiotic, anti-proliferative inhibitors, enzymes, hormones, etc. However, the prepared systems lack versatility, and are not able to be adjusted to several drugs as well as pathologies unlike the ocular insert embodying the invention.

The knowledge of the properties of the involved materials (polymers and drugs) is essential for the development of new drug delivery systems. Despite the invested effort in the development of new polymers, researchers still face many obstacles, including the immobilization of bioactive macromolecules such as proteins. However, the potential demonstrated by polymers, whose properties can easily be shaped according to the desired functions, indicates that these materials will continue to play a key role in the development of systems for controlled drug release.

There are still some gaps that the current ocular CDDS cannot fulfil such as the simultaneous loading with two or more drugs and their release during different time periods, at distinct rates and profiles. The ocular insert embodying the invention intends to fill those gaps while improving the patient compliance to the different therapeutics by reducing the foreign body sensation and facilitating its placement in the eye.

REFERENCES

[1] Patton T F, Robinson J L, "Quantitative precorneal disposition of topically applied pilocarpine nitrate in rabbit eyes", J. Pharm. Sci., vol. 65, pp. 1295-301, 1976.

[2] Wood R W, Li V H K, Kreuter L, Robinson J R, "Ocular disposition of poly-hexyl-2-cyano[3-14C]acrylate nanoparticles in the albino rabbit", Int. J. Pharm., vol. 23, pp. 175-183, 1985.

[3] Lim J I, Wolitz R A, Dowling A H, Bloom H R, Irvine A R, Schwartz D M, "Visual and anatomic outcomes associated with posterior segment complications after ganciclovir implant procedures in patients with AIDS and cytomegalovirus retinitis", Am. J. Ophthalmol., vol. 127, n.° 3, pp. 288-293, 1999.

[4] Shell J W, Baker R., "Diffusional systems for controlled release of drugs to the eye", Ann. Ophthalmol., vol. 6, n.° 10, pp. 1037-44, 1974.

[5] Bawa R, "Sustained-release formulation containing an amino acid polymer", U.S. Pat. No. 4,668,506, 26 May 1987.

[6] Bawa R, Deichert W G, "Sustained-release formulation containing an amino acid polymer with a lower alkyl (C1-C4) polar solvent", U.S. Pat. No. 4,713,244, 12 Dec. 1987.

[7] Bawa R, Ruscio D, "Sustained release formulation containing an ion-exchange resin", U.S. Pat. No. 4,931,279, 5 Jun. 1990.

[8] Alvarez-Lorenzo C, Yañez F, Barreiro-Iglesias R, Concheiro A, "Imprinted soft contact lenses as norfloxacin delivery systems", J. Control. Release, vol. 113, n.° 3, pp. 236-244, 2006.

[9] Costa V P, Braga M E M, Duarte C M M, Alvarez-Lorenzo C, Concheiro A, Gil M H, de Sousa H C, "Anti-glaucoma drug-loaded contact lenses prepared using supercritical solvent impregnation", J. Supercrit. Fluids, vol. 53, n.° 1-3, pp. 165-173, 2010.

[10] Ferreira J A, Oliveira P, Silva P M, Carreira A, Gil M H, J. N. Murta, "Sustained Drug Release from Contact Lenses", CMES, vol. 60, n.° 2, pp. 151-179, 2010.

[11] Gulsen D, Chauhan A, "Ophthalmic Drug Delivery through Contact Lenses", Invest. Ophthalmol. Vis. Sci., vol. 45, n.° 7, pp. 2342-2347, 2004.

[12] Urquhart J., "Development of the Ocusert pilocarpine ocular therapeutic systems case history in ophthalmic product development", in Ophthalmic Drug Delivery Systems (J. R. Robinson, ed), Washington, D.C., American Pharmaceutical Association, 1980.

[13] Armali M F, Rao K R, "The Effect of Pilocarpine Ocusert® with Different Release Rates on Ocular Pressure", Invest. Ophthalmol., vol. 12, n.° 7, pp. 491-496, 1973.

[14] Place V A, Fisher M, Herbst S, Gordon L, Merrill R, "Comparative Pharmacological Effects of Pilocarpine Administered to Normal Subjects by Eyedrops or by Ocular Therapeutic Systems", Am. J. Ophthalmol., vol. 80, n.° 4, pp. 706-712, 1975.

[15] Brown H S, Meltzer G, Merrill R C, Fisher M, Ferre C, Place V A, "Visual Effects of Pilocarpine in Glaucoma. Comparative Study of Administration by Eyedrops or by Ocular Therapeutic Systems", Arch. Ophthalmol., vol. 94, n.° 10, pp. 1716-22, 1976.

[16] Wentworth J S, Paterson C A, Wells J T, Tilki N, Gray R S, McCartney M D, "Collagen shields exacerbate ulceration of alkali-burned rabbit corneas", Arch. Ophthalmol., vol. 111, n.° 3, pp. 389-92, 1993.

[17] Mitra A K, Ophthalmic Drug Delivery Systems, New York: Marcel Dekker, Inc, 1992.

[18] Katz J L, Kaufman H E, Breslin C, Katz I M, "Slow-release artificial tears and the treatment of keratitis sicca", Ophthalmology, vol. 85, n.° 8, pp. 787-99, 1978.

[19] Lamberts D W, Langston D, Chu W, "A clinical study of slow-releasing artificial tears", Ophthalmology, vol. 85, n.° 8, pp. 794-800, 1978.

[20] LaMotte L, Grossman E, Hersch J, "The efficacy of cellulosic ophthalmic inserts for treatment of dry eye", J. Am. Gptom. Assoc., vol. 56, n.° 4, pp. 198-205, 1985.

[21] Marmer RH, "Therapeutic and protective properties of the corneal collagen shield", J. Cataract Refract. Surg., vol. 14, n° 5, pp. 496-509, 1988.

[22] Bloomfield S E, Miyata T, Dunn M W, Bueser N, Stenzel K H, Rubin A L., "Soluble gentamicin ophthalmic inserts as drug delivery system", Arch. Ophthalmol., vol. 96, n° 5, pp. 885-93, 1978.

[23] Slatter D H, Costa N D, Edwards M E, "Ocular inserts for application of drugs to bovine eye—in vivo and in vitro studies on the release of gentamicin from collagen inserts", Aust. Vet. J., vol. 59, n° 1, pp. 4-6, 1982.

[24] Punch P L, Slatter D H, Costa N D, Edwards M E, "Ocular inserts for application of drugs to bovine eyes—in vitro studies on gentamicin release from collagen inserts", Aust. Vet. J., vol. 62, n° 3, pp. 79-84, 1985.

[25] Peiffer R L, Safrit H D, White E, Eifrig D E, "Intraocular response to cotton, collagen and cellulose in the rabbit", Ophthalmic Surg., vol. 14, n° 7, pp. 582-7, 1983.
[26] Aquavella J V, Ruffini J L, LoCascio J A, "Use of collagen shields as a Surgical adjunct", J. Cataract Refract. Surg., vol. 14, n.° 5, pp. 492-9, 1988.
[27] Smith R L, "Ophthalmic compositions of carbonic anhydrase inhibitors for topical application in the treatment of elevated intraocular pressure", U.S. Pat. No. 4,438,123, 20 Mar. 1984.
[28] Bhushan R, "Ophthalmic formulation for the prevention and treatment of ocular conditions", European Patent 1972344 A1, 24 Sep. 2008.
[29] Saettone M F, Giannaccini B, Chetoni P, Galli G, Chiellini E, "Vehicle Effects in Ophthalmic Bioavailability: An Evaluation of Polymeric Inserts Containing Pilocarpine", J. Pharm. Pharmacol., vol. 36, n.° 4, pp. 229-42, 1984.
[30] Chiellini E, Saettone M F, "Polymer Drug Delivery System in Ophthalmic Applications", J. Bioact. Compact. Polym., vol. 3, n° 1, pp. 86-93, 1988.
[31] Gevariya H, Dharamsi A, Girhepunje K, Pal R, "Once a day ocular inserts for sustained delivery of levofloxacin: Design, formulation and evaluation", Asian J Pharmaceutics, pp. 314-318, October-December 2009.
[32] Khurana G, Arora S, Pawar P K, "Ocular insert for sustained delivery of gatifloxacin sesquihydrate: Preparation and evaluations", Int. J. Pharm. Investig., Vol. 2, n° 2, pp. 70-77, 2012.
[33] Jethava J K, Jethava G K, "Design, formulation and evaluation of novel sustain release bioadhesive in-situ gelling ocular inserts of ketorolac tromethamine", Int. J. Pharm. Investig., vol. 4, n° 4, pp. 226-232, 2014.
[34] De Souza J F, Maia K N, Patricio P S O, Fernandes-Cunha G M, Da Silva M G, Jensen C E M, Silva G R, "Ocular inserts based on chitosan and brimonidine tartrate: Development, characterization and biocompatibility", J. Drug Deliv. Sci. Technol., vol. 32, pp. 21-30, 2016.

SUMMARY OF THE INVENTION

The present invention concerns a biocompatible ocular insert with polymeric composition, designed for "in vivo" sustained drug release to be applied in the treatment of different ocular pathologies.

The currently available technologies for ocular drug delivery present several limitations which include at least one of the listed below.

Short residence time of the drugs in the eye;
Fluctuations of the drug concentration (namely with eye drops);
Low compliance of the patient to the therapeutics;
Short release periods (from 1 to 7 days);
Insert dislodgment;
High costs involved in the insert preparation;
"Fickian" drug delivery profile (with high release rates registered during the first period of time followed by a pronounced decrease of rate release);
The available systems comprise only one drug and are therefore directed to a single pathology.

The present invention refers to a new controlled drug delivery system (CDDS) with a polymer-based composition, applicable to a variety of drugs and other compounds to be applied in the treatment of different ocular pathologies. This system allows releasing these drugs under suitable concentration levels during suitable periods of time. The device may be inserted in the lower or upper fornix conjunctiva, in a non-invasive way, (FIG. 1) meaning that the patient will be able to place the device himself, without intervention of medical specialized staff. For this reason, the polymeric material will have specific physicochemical properties and the device size and shape were designed to avoid expulsion or breaking as well as to minimize the foreign body sensation.

This invention will release the drug in such controlled rate that will allow the drug release for time periods of up to 6 months by either a "Fickian" or a linear profile according to the intend purpose/pathology.

The insert can be prepared with different shapes (spherical or hemispherical) and/or architectures (monolithic/layered either with or without a drug core), allowing the incorporation of at least one drug which can be released at different rates. The size, shape and design of the insert is adjusted in order to tune the drug(s) delivery profile(s) and to inhibit the risk of displacement or expulsion.

BRIEF DESCRIPTION OF DRAWINGS

Further characteristics and advantages of the ocular insert according to the present invention will be more apparent from the following description of some embodiments thereof, made as a non-limiting examples, with reference to the appended drawings wherein.

Figure Captions:
1—Ocular insert embodying the invention.
2—Upper eye lid.
3—Lower eye lid.
4—Conjunctiva.
5—Front view of different shapes of the ocular insert embodying the invention.
6—Top view of different shapes of the ocular insert embodying the invention.
7—Rotate views of different shapes of the ocular insert embodying the invention.
8—Central core containing the drug or drugs incorporated in the ocular insert embodying the invention.
9—Polymer-based layer involving the central core of the ocular insert embodying the invention.
10—Monolithic design of the ocular insert embodying the invention where the drug or drugs are homogenously dispersed on a polymer-based matrix.
11—Polymer-based layer containing or not a dispersed drug composing the ocular insert embodying the invention.

DETAILED DESCRIPTION OF THE DRAWINGS

Figure 1:
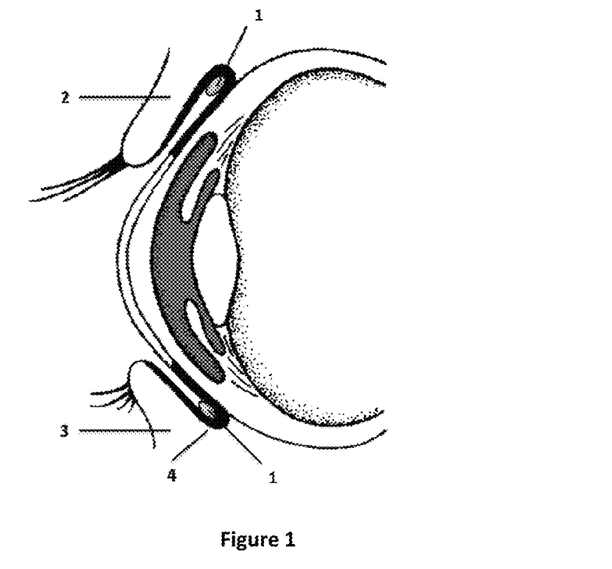
FIG. 1 shows the schematic representation of the sagittal cross-section of the eye as well as the insert's possible application sites in the upper or lower fornix conjunctiva.

FIG. 1 shows the schematic representation of the sagittal cross-section of an eye. The ocular insert embodying the invention is also represented in both possible application sites: upper or lower fornix conjunctiva. In either case, its placement can be done by the patient himself as it is not an invasive procedure.

Figure 2:
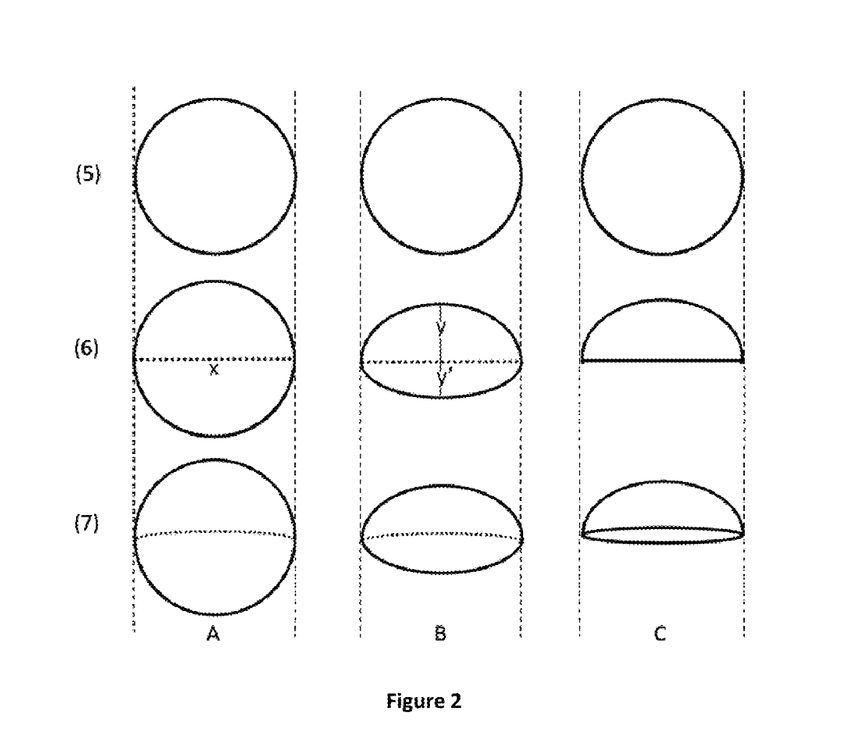
FIG. 2 shows diagrammatically the front (5), top (6) and rotate views (7) of different shapes of the ocular insert device embodying the invention.

FIG. 2 shows the possible range of shapes that the ocular insert embodying the invention has. From a complete spherical shape (A) to a hemisphere (C) the diameter, x, varies from 2.0 mm up to 8.0 mm. The shape can be asymmetric (B) with the larger radius, y, varying from 0.5 mm up to 4.0 mm and the smaller radius, y', varying from 0.0 mm up to 4.0 mm. For each individual ocular insert the value of y' never exceeds the value of y and the value of y never exceed half of x value and the value of x never exceeds 8.0 mm, which can be expressed by the formulas $y' \leq y$; $y \leq x/2$ and $x \leq 8.0$ mm. Therefore the larger ocular insert embodying the invention is a sphere of 8.0 mm diameter and the smallest is a dome-shaped hemisphere of 2.0 diameter with a height of 0.5 mm.

Figure 3:
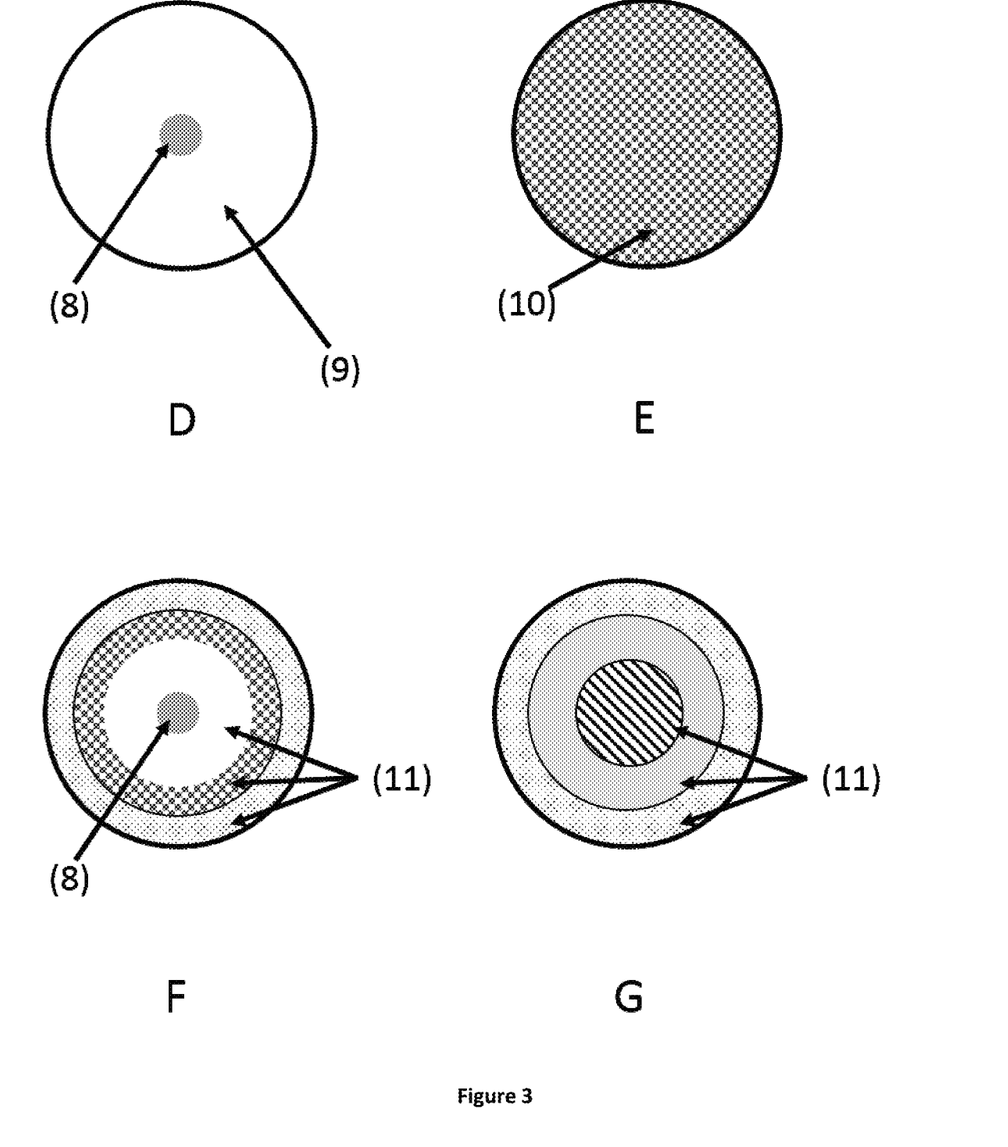
FIG. 3 shows diagrammatic sectional views of the ocular insert device embodying the invention containing at least one drug in a central core and/or dispersed in one or more layers.

FIG. 3 shows the possible designs, architectures and constructs that the ocular insert embodying the invention can be made of. Diagram D shows the ocular insert embodying the invention with a central core (8) containing the drug or drugs surrounded by a polymer-based layer (9). Diagram E shows the ocular insert embodying the invention with a monolithic design where the drug or drugs are homogenously dispersed on a polymer-based matrix (10). Diagram F shows a combination of the previous diagrams, where the ocular insert embodying the invention has the drugs in a central core (8) and dispersed in different layers (11). Diagram G shows the ocular insert embodying the invention where the drugs are dispersed in different layers. Each of the layers shown in Diagrams F and G can be made of different polymers or combination of polymers and can contain different drugs and/or different concentrations of the same drug. The number of polymeric layers and of immobilized drugs, the amount of each drug and the immobilization technique depends on the therapeutic application, i.e., on the intended drug(s) release profile(s).

Figure 4:
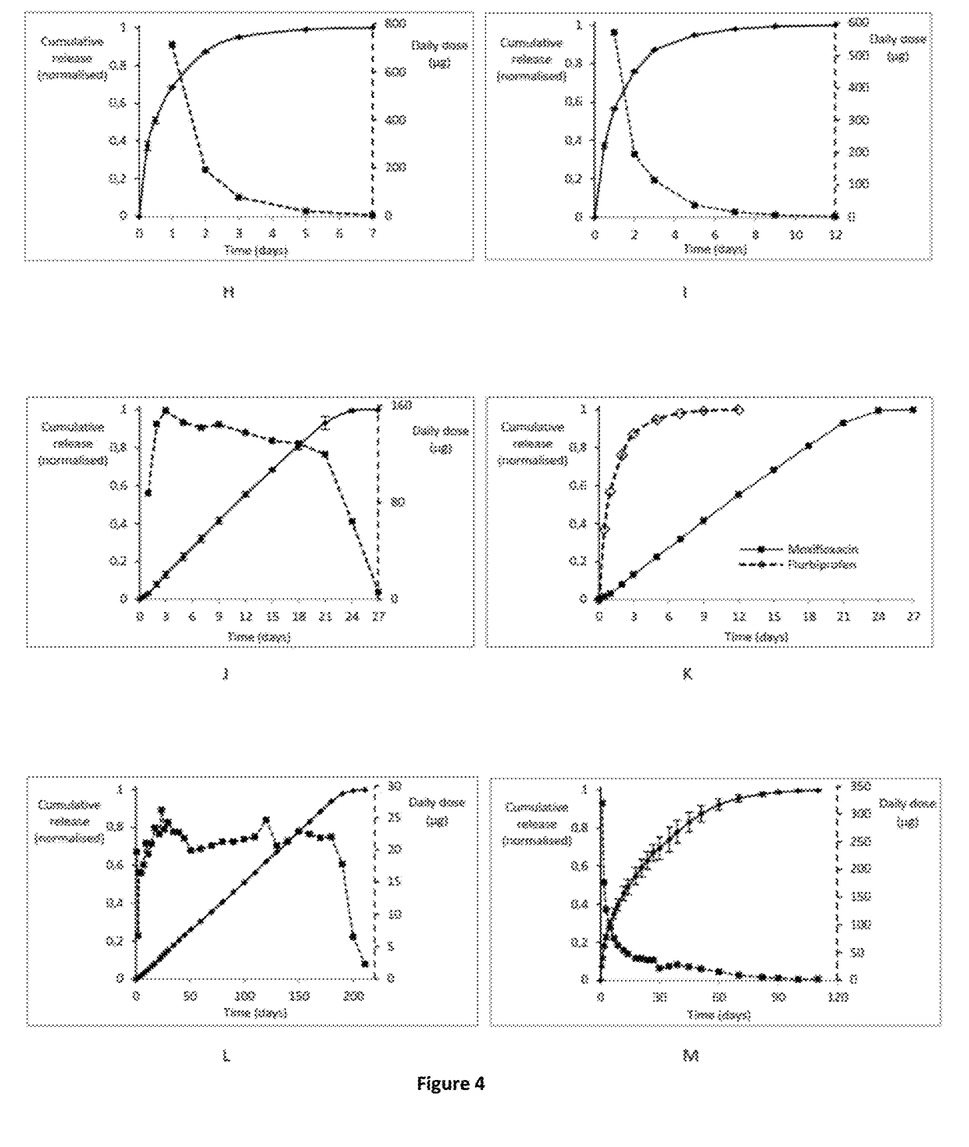
FIG. 4 shows different release profiles of various drugs from the ocular insert embodying the invention during up to 200 days and the corresponding daily dosage. To obtain these profiles different architecture, shapes, sizes and different chemical compositions of the device embodying the invention were used.

FIG. 4 shows the release profiles of various drugs obtained from ocular inserts embodying the invention constructed with distinct architectural features and from different compositions. Release profile from example 1 shows a "Fickian" release profile of a drug for a period of 7 days, with the daily dose decreasing dramatically during the first 3 days. Release profile from example 2 has the same release mechanism as example 1 but for a different drug and for a slightly longer period of time. In example 6, with an ocular insert embodying the invention that is larger than examples 1 and 2, the release is extended up to 110 days. Release profile from example 3 shows a linear drug release for up to 21 days with an almost constant daily dosage drug delivery. Longer but still constant releases can be obtained by changing the size of the insert and the amount of drug in the central core, reaching almost 200 days as in example L. Other examples are shown to demonstrate the versatility and novelty of the invention in respect to the drug release profiles that can be obtained in a tailor-made mode, changing the composition, shape and architecture of the ocular insert embodying the invention.

DETAILED DESCRIPTION OF THE INVENTION

The present invention concerns a polymer-based ocular insert for drug delivery by non-invasive insertion into the upper or lower fornix conjunctiva of the eye characterized in that the ocular insert has a spherical or spherical dome shape, comprises at least one polymeric layer with or without a drug core and allows the sustained release of at least one drug up to 300 days of release time.

In a preferred embodiment of the invention, the polymeric composition comprises a polyester, such as polycaprolactone, poly(lactic acid), poly(glycolic acid) or their copolymers and a polyol, such as polyethylene glycol, castor oil or poly(vinyl alcohol), the polyol content in the final mixture varying from 0% to 50%.

In a more preferred embodiment, the polymeric composition comprises polycaprolactone (PCL) and polyethylene glycol (PEG) or copolymers thereof, the molecular weight of PCL varying from 500 up to 30,000 and the molecular weight of PEG varying from 200 up to 40,000.

In an even more preferred embodiment, the polymeric composition comprises a copolymer of PCL-PEG in which the content of PEG varies from 10% to 30%.

In another preferred embodiment, the polymeric composition further contains crosslinkers, such as acrylates or cyanates, and plasticizers, such as adipates, phthalates, polymers or solvents.

In another preferred embodiment, the insert comprises at least one layer of a polymer-based matrix where at least one drug is dispersed, a central core of at least one drug surrounded by a polymeric layer, or combinations thereof.

In another preferred embodiment, at least one drug is preferably completely released during a period of time that could vary from 7 to 200 days with a linear or "Fickian" diffusion rate. This means that the invention may either be prepared as an insert that releases the entire drug after 7 days, or prepared as in insert that releases entirely that same drug or other after 200 days, or during periods of time between 7 to 200 days.

In an even more preferred embodiment, the insert allows the full release of at least two drugs, either at the same or different rates.

In another preferred embodiment, the ocular insert has a length from 2 mm to 8 mm and a width from 0.5 to 8 mm.

In a more preferred embodiment, the ocular insert is a sphere of 8.0 mm diameter.

In another more preferred embodiment, the ocular insert is a dome-shaped hemisphere with a diameter of 2.0 mm and a height of 0.5 mm.

In another preferred embodiment, the drug release mechanism is diffusion, osmosis, bioerosion or combination of any of the processes.

In another preferred embodiment, at least one drug is chosen from antibiotics, such as tetracycline, chlortetracycline, bacitracin, neomycin, polymyxin, gramicidin, cephalexin, oxytetracycline, chloramphenicol, kanamycin, rifampicin, gentamycin, erythromycin, penicillin and fluoroquinolones; antibacterials such as sulfonamides, sulfadiazine, sulfacetamide, sulfamethiazole and sulfisoxazole, nitrofurazone and sodium propionate; antivirals including idoxuridine, trifluorothymidine, acyclovir, ganciclovir and interferon; anti-allergenics such as sodium cromoglycate, antazoline, methapyriline, chlorpheniramine, cetirizine and prophenpyridadine; anti-inflammatories such as hydrocortisone, hydrocortisone acetate, dexamethasone, dexamethasone 21-phosphate, fluocinolone, medrysone, prednisolone acetate, fluoromethalone, betamethasone, triamcinolone, flurbiprofen and other non-steroidal anti-inflammatory drugs; decongestants such as phenylephrine, naphazoline and tetrahydrozoline; miotics and anticholinesterase such as pilocarpine, acetylcholine chloride, physostigmine, eserine, carbachol, di-isopropyl fluorophosphate, phospholine iodine, and demecarium bromide; mydriatics such as atropine sulfate, cyclopentolate, homatropine, scopolamine, tropicamide, eucatropine, and hydroxyamphetamine; sympathomimetics such as epinephrine; immunological drugs such as vaccines and immune stimulants; hormonal agents such as estrogens, estradiol, progestational, progesterone, insulin, calcitonin, parathyroid hormone and peptide, vasopressin, hypothalamus releasing factor; beta adrenergic blockers such as timolol maleate, levobunolol HC1 and betaxolol HC1; growth factors such as epidermal growth factor and fibronectin; carbonic anhydrase inhibitors such as dichlorphenamide, acetazolamide and methazolamide and other drugs such as prostaglandins, antiprostaglandins, and prostaglandin precursors or analogues and mixtures thereof.

The invention also concerns a process of manufacturing the ocular insert by customizing the desired releasing rate by defining the drugs concentrations, the polymer composition, the thickness of each layer and the thickness of the entire device.

In a preferred embodiment, the process of the invention further comprises the steps of I) obtaining a central core of at least one drug surrounded by a polymeric layer:

a—the drug is compressed either alone or with a small amount of polymer or aggregator to form a mini tablet;

b—each layer is generated by covering the previous (inner) layer of the insert being created with a mixture of melted polymer and drug; this mixture is adjusted according to the required release profile; the layer thickness is defined by the amount of the mixture and the radius of the insert already formed;

c—the drug or drugs are mixed with the melted polymer by stirring, controlling the cooling and the stirring of the mixture until a homogenous solid or gel-like compound is obtained; or II) obtaining a monolithic polymer-based matrix where the at least one drug is dispersed by molding or hot-melt extrusion; or III) combining steps I and II.

In the area of ophthalmology, the conventional method of drops topical application involves repeated administrations of the drugs solutions and the drugs concentration profiles are characterized by extreme fluctuations with an excessive concentration stage, followed by a brief period of correct dose and ending in a long under dosing period. Moreover, it is necessary to take into consideration the drainage of the lacrimal film and the small corneal permeability which require the use of high doses of drug in order to secure the intraocular therapeutic level. Since only 1 to 3% of the drug penetrates the cornea and the remainder is absorbed by systemic routes, high concentrations can bring toxicity associated side effects at a systemic level. To overcome these obstacles, many polymers have been used both in ophthalmic preparations and in solid drug delivery systems.

Preparation of systems that release drug in a predictable and reproducible at a specific location and for a long period of time has much merit, since drug delivery is dependent on many factors, including the concentration and physical and chemical properties of the drug, the time of contact with the biological system, and also on the mechanical, physical, chemical, and biochemical features of the drug carrier. Ideally a drug delivery system provides the drug only when and where it is needed and within the appropriate concentration for the desired therapeutic effect. Therefore, it is desirable to control the release of the pharmacological agent to maintain the drug concentration above the minimal effective concentration (MEC) and below the minimal toxic concentration (MTC). This concentration interval is known as the therapeutic range.

Ocular CDDS allow therapeutic agents to be available in the eye for extended periods of time at the desired concentrations. Furthermore, the following advantages when compared to conventional eye drop treatment should also be considered:

Lower systemic toxicity, since lower amounts of drug are used when comparing to the eye drops treatment and also the fact that this form of treatment is targeted to the eye where it stays for longer time;

Improved patient compliance, namely for treatment of chronic diseases, such as glaucoma, as drug administration frequency is significantly reduced;

Improved safety, as accurate dosing is achieved;

Better product stability as drugs are in dried state;

No need for preservatives that could generate inflammatory reactions.

Despite these advantages, the ocular inserts currently available present some limitations:

Low compliance of the patient to the therapeutics due to the difficulty on the application of the dosage form;

Short release periods (from 1 to 7 days);

Insert dislodgment;

High costs involved in the insert preparation;

"Fickian" drug delivery profile (with high drug release rates registered during the initial stage followed by a pronounced decrease of rate release).

The available systems comprise only one drug and are therefore directed to a single pathology.

The present invention refers to a new polymer-based controlled drug delivery system (CDDS) applicable to a variety of drugs and other compounds to be applied in the treatment of different ocular pathologies. The device embodying the invention allows the release of multiple drugs at controlled concentration levels during suitable periods of time. This allows the simultaneous administration of different drugs from 1 week to 6 months by either a "Fickian" or a linear profile according to the intended purposes/pathologies and by using just one device.

The device is placed by a non-invasive procedure and may be inserted in the lower or upper fornix conjunctiva, meaning that the patient will be able to place the insert by himself with no intervention of specialized medical staff. Therefore, the polymeric material will have specific physicochemical properties and the device size and shape are designed to avoid displacement, expulsion or breaking and to minimize the foreign body sensation. The range of possible shapes of the insert is represented in FIG. 2 and may vary from a spherical shape (A) to a hemisphere (C). Considering the diameter, x, its value may vary from 2.0 mm up to 8.0 mm. The shape can also be asymmetric (B) with the larger radius, y, varying from 0.5 mm up to 4.0 mm and the smaller radius, y', varying from 0.0 mm up to 4.0 mm. For each individual ocular insert the value of y' never exceeds the value of y and the value of y never exceeds half of x value and the value of x never exceeds 8.0 mm. These features can be expressed by the formulas $y' \leq y$; $y \leq x/2$ and $x \leq 8.0$ mm. Therefore, the larger ocular insert device embodying the invention is a sphere of 8.0 mm diameter and the smallest is a dome-shaped hemisphere of 2.0 diameter with a height of 0.5 mm. The simultaneously and customized release profiles of multiple drugs are obtained by using different shapes (spherical or hemispherical) and/or architectures (monolithic/layered either with or without a drug core). The amounts of the drugs immobilized in the ocular insert device embodying the invention are set based on the duration of the treatment and the recommended daily dose of each drug. Both the duration and the daily dose, are gathered from the state of the art for each specific disease therapeutics. Therefore, the quantity of each drug loaded into the ocular insert embodying the invention varies from few micrograms to several milligrams. The maximum drug load capacity of the ocular insert embodying the invention depends on the drug solubility in the melted polymer, the size of the device and the intended release profile. Short term releases requires less drug quantity than long-terms release devices. Constant, linear releases are obtained when the drug is entrapped in a central core allowing a large quantity of drug to be compressed into a small tablet as shown in FIG. 3A. This architecture was used to obtain the release profiles shown in FIGS. 4J, 4K, 4L, 4N and 4Q.

On the other hand for a "Fickian" release design (as the ones presented in FIG. 4H, 4I, 4K, 4M, 4O, 4P and 4R), the drug must be homogeneously dispersed into a monolithic device as shown in FIG. 3B. Here, the amount of dispersed drug is limited by the drug solubility in the melted polymer and by the ratio drug/polymer where the properties and integrity of the device must not be compromised by the presence and subsequent release of a large amount of drug. More complex drug release profiles are obtained by producing multilayered systems with or without a central drug core as represented in FIGS. 3C and 3D. Due to different designs and architectures there are distinct manufacturing processes to produce the ocular insert device embodying the invention:
- to obtain a central core the drug must be compressed either alone or with a small amount of polymer or aggregator to form a mini tablet;
- each layer is generated by covering the previous (inner) layer of the device being created with a mixture of melted polymer and drug. This mixture is adjusted according to the required release profile where the amount of drug and of polymer, the polymer composition and the proportion drug/polymer is specific for each layer. The layer thickness is defined by the amount of the mixture and the radius of the device already formed;
- the drug or drugs are mixed with the melted polymer by stirring. In those cases where the solubilization of the drug is not possible (either due to the physical and chemical properties or to the ratio drug/polymer) the homogeneity of the suspension is obtained by controlling the cooling and the stirring of the mixture until a homogenous solid or gel-like compound is obtained;
- For the ocular insert embodying the invention made of one layer, i.e., a monolithic system, the manufacturing process is simpler and involves techniques such as molding or hot-melt extrusion;

The polymers used are preferably polycaprolactone (PCL), polyethyleneglycol (PEG), co-polymers PEG-PCL and mixture of any of the above-mentioned in any proportion. The molecular weight of PCL may vary from 500 up to 30,000 and that of PEG from 200 up to 40,000.

For further tune of the chemical, physical and mechanical properties of the ocular insert embodying the invention different crosslinkers such as acrylates, cyanates among others and plasticizers such as adipates, phthalates, polymers, solvents among others can be used.

EXAMPLE 1

A formulation of the ocular insert embodying the invention, Formulation 1, was prepared as follows: The copolymer used in this formulation was a low molecular weight polycaprolactone/polyethelyneglycol in a ratio of 75/25 (PCL/PEG; mass/mass). The drug moxifloxacin was mixed with the copolymer in a beaker under magnetic stirring at 70° C. for a few minutes. The drug percentage regarding the total mixture weight was 2% (mass/mass).

The ocular inserts embodying the invention were then prepared from that drug/polymer mixture with asymmetrical shape as represented in scheme B of FIG. 2. The average length of the large diameter was 5.8 mm while the small diameter measured 2.7 mm. The average weight of the ocular inserts of Formulation A was approximately 50 mg with approximately 1 mg of drug dispersed in the polymeric matrix.

Each insert of Formulation 1 was placed in phosphate-buffered saline solution (PBS) at 37° C. until all the drug was released to the aqueous media. The moxifloxacin dissolved was quantified by an UV-Vis spectrophotometric method and the results shown a "Fickian" release where approximately 50% of the drug was released in the initial 12 hours and almost all of the entrapped drug was dissolved at day 3 of the dissolution study (FIG. 4H).

EXAMPLE 2

A formulation of the ocular insert embodying the invention, Formulation 2, is similar to Formulation 1 except that the drug entrapped in the polymer matrix was flurbiprofen instead of moxifloxacin.

The architecture, size and shape are the same applied on formulation 1. Therefore the average weight of the ocular inserts of Formulation 2 was also approximately 50 mg with approximately 1 mg of drug dispersed in the polymeric matrix. Each insert of Formulation 2 was placed in phosphate-buffered saline solution (PBS) at 37° C. until all the drug was released to the aqueous media. The flurbiprofen dissolved was quantified by an UV-Vis spectrophotometric method and the results shown a "Fickian" release where approximately 50% of the drug was released in the initial 24 hours and almost all of the entrapped drug was dissolved at day 5 of the dissolution study (FIG. 4I).

EXAMPLE 3

A formulation of the ocular insert embodying the invention, Formulation 3, was prepared as follows: The copolymer used in this formulation was a low molecular weight polycaprolactone/polyethelyneglycol in a ratio of 75/25 (PCL/PEG; mass/mass). 100 mg of Moxifloxacin was slightly compressed under 300 mbar for half a minute to form a tablet from which small portions of 3 mg were obtained. Each of these small tablets were then covered with melted copolymer to form the final ocular insert devices embodying the invention.

These ocular inserts embodying the invention in Formulation 3 were of an asymmetrical shape as represented in scheme B of FIG. 2. The average length of the large diameter was 5.8 mm while the small diameter measured 2.7 mm. The average weight of the ocular inserts of Formulation 3 was 50 mg with approximately 3 mg of drug in a central core.

Each insert of Formulation 3 was placed in phosphate-buffered saline solution (PBS) at 37° C. until all the drug was released to the aqueous media. The moxifloxacin dissolved was quantified by an UV-Vis spectrophotometric method and the results shown a constant drug release for up 21 days, when more than 90% of moxifloxacin was already dissolved (FIG. 4J). This release rate corresponds to an ocular daily dose that varies from 120 to 160 μg of drug, considering the lacrimal film turnover.

EXAMPLE 4

A formulation of the ocular insert embodying the invention, Formulation 4, was prepared combining the procedures of Formulation 2 and 3, which allowed the entrapment of two different drugs in two distinct ways—moxifloxacin in a central core and flurbiprofen dispersed in the polymer matrix.

These ocular inserts embodying the invention in Formulation 4 were of an asymmetrical shape as represented in scheme B of FIG. 2. The average length of the large diameter was 5.8 mm while the small diameter measured 2.7 mm. The average weight of the ocular inserts of Formulation 4 was 50 mg with approximately 3 mg moxifloxacin in a central core and 1 mg of flurbiprofen dispersed in the polymeric matrix.

Each insert of Formulation 4 was placed in phosphate-buffered saline solution (PBS) at 37° C. until both drugs were totally released to the aqueous media. The amount of both drugs dissolved was quantified by an UV-Vis spectrophotometric method and the results shown a constant moxifloxacin release for up 21 days, when more than 90% was already dissolved, and a "Fickian" flurbiprofen release where approximately 50% of the drug was released in the initial 24 hours and almost all of the entrapped flurbiprofen was dissolved at day 5 of the dissolution study (FIG. 4K).

EXAMPLE 5

A formulation of the ocular insert embodying the invention, Formulation 5, was prepared as follows: The copolymer used in this formulation was a low molecular weight polycaprolactone/polyethelyneglycol in a ratio of 80/20 (PCL/PEG; mass/mass). 100 mg of Moxifloxacin was slightly compressed under 300 mbar for 30 sec to form a tablet from which small portions of 4 mg were obtained. Each of these small tablets were then covered with melted copolymer to form the final ocular insert embodying the invention.

These ocular inserts embodying the invention in Formulation 5 were of spherical shape as represented in scheme A of FIG. 2 with an average diameter of approximately 7 mm. The average weight of the ocular inserts of Formulation 5 was approximately 150 mg with approximately 4 mg of drug in a central core.

Each insert of Formulation 5 was placed in phosphate-buffered saline solution (PBS) at 37° C. until all the drug was released to the aqueous media. The moxifloxacin dissolved was quantified by an UV-Vis spectrophotometric method and the results shown a constant drug release for up to 190 days, when more than 90% of moxifloxacin was already dissolved (FIG. 4L). This release rate corresponds to an ocular daily dose between 15 and 25 μg of drug, considering the lacrimal film turnover.

EXAMPLE 6

A formulation of the ocular insert embodying the invention, Formulation 6, was prepared as follows: The copolymer used in this formulation was a low molecular weight polycaprolactone/polyethelyneglycol in a ratio of 80/20 (PCL/PEG; mass/mass). Moxifloxacin was mixed with the copolymer in a beaker under magnetic stirring at 70° C. for a few minutes. The drug percentage regarding the total mixture weight was 1.3% (mass/mass).

Ocular inserts embodying the invention were then prepared from that drug/polymer mixture with of spherical shape as represented in scheme A of FIG. 2 with an average diameter of 6.4 mm. The average weight of the ocular inserts of Formulation M was approximately 150 mg with approximately 2 mg of drug dispersed in the polymeric matrix.

Each insert of Formulation 6 was placed in phosphate-buffered saline solution (PBS) at 37° C. until all the drug was released to the aqueous media. The moxifloxacin dissolved was quantified by an UV-Vis spectrophotometric method and the results shown a "Fickian" release where approximately 50% of the drug was released in the initial 15 days and almost 90% of the entrapped drug was dissolved at day 60 of the dissolution study (FIG. 4M).

EXAMPLE 7

A formulation of the ocular insert embodying the invention, Formulation 7, was prepared as follows: The copolymer used in this formulation was a low molecular weight polycaprolactone/polyethelyneglycol in a ratio of 80/20 (PCL/PEG; mass/mass). 100 mg of Moxifloxacin was slightly compressed under 300 mbar for half a minute to form a tablet from which small portions of 2 mg were obtained. Each of these small tablets were then covered with melted copolymer to form the final ocular insert devices embodying the invention.

These ocular inserts embodying the invention in Formulation 7 were of spherical shape as represented in scheme A of FIG. 2 with an average diameter of 5.7 mm. The average weight of the ocular inserts of Formulation 7 was approximately 100 mg with approximately 2 mg of drug in a central core.

Each insert of Formulation 7 was placed in phosphate-buffered saline solution (PBS) at 37° C. until all the drug was released to the aqueous media. The moxifloxacin dissolved was quantified by an UV-Vis spectrophotometric method and the results shown a constant drug release for up 130 days, when more than 90% of moxifloxacin was already dissolved (FIG. 4N). This release rate corresponds to an ocular daily dose of approximately 15 μg of drug, considering the lacrimal film turnover.

EXAMPLE 8

A formulation of the ocular insert embodying the invention, Formulation 8, was prepared as follows: The copolymer used in this formulation was a low molecular weight polycaprolactone/polyethelyneglycol in a ratio of 70/30 (PCL/PEG; mass/mass). This copolymer was then cross-linked with 5% (m/m) of hexamethylene diisocyanate. Moxifloxacin was mixed with the copolymer in a beaker under magnetic stirring at 70° C. for a few minutes. The drug percentage regarding the total mixture weight was 1% (mass/mass).

Ocular inserts embodying the invention were then prepared from that drug/polymer mixture with asymmetrical shape as represented in scheme A of FIG. 2 with an average diameter of 5.7 mm. The average weight of the ocular inserts of Formulation 8 was approximately 100 mg with approximately 1 mg of drug dispersed in the polymeric matrix.

Each insert of Formulation 8 was placed in phosphate-buffered saline solution (PBS) at 37° C. until all the drug was released to the aqueous media. The moxifloxacin dissolved was quantified by an UV-Vis spectrophotometric method and the results shown a "Fickian" release where approximately 50% of the drug was released in the initial 3 days and almost all of the entrapped drug was dissolved at day 21 of the dissolution study (FIG. 4O).

EXAMPLE 9

A formulation of the ocular insert embodying the invention, Formulation 9, was prepared as follows: The copolymer was prepared in a ratio of 90/10 (PCL/PEG; mass/mass) using a low molecular weight polycaprolactone and a high molecular weight polyethelyneglycol (35,000 g/mol). This copolymer was then crosslinked with 5% (m/m) of hexamethylene diisocyanate. Moxifloxacin was mixed with the copolymer in a beaker under magnetic stirring at 80° C. for a few minutes. The drug percentage regarding the total mixture weight was 1% (mass/mass).

The ocular inserts embodying the invention were then prepared from that drug/polymer mixture with asymmetrical shape as represented in scheme A of FIG. 2 with an average diameter of 5.7 mm. The average weight of the ocular inserts of Formulation 9 was approximately 100 mg with approximately 1 mg of drug dispersed in the polymeric matrix.

Each insert of Formulation 9 was placed in phosphate-buffered saline solution (PBS) at 37° C. until all the drug was released to the aqueous media. The moxifloxacin dissolved was quantified by an UV-Vis spectrophotometric method and the results shown a "Fickian" release where approximately 50% of the drug was released in the initial 12 days and almost all of the entrapped drug was dissolved at day 80 of the dissolution study (FIG. 4P).

EXAMPLE 10

A formulation of the ocular insert embodying the invention, Formulation 10, was prepared as follows: The copolymer used in this formulation was a low molecular weight polycaprolactone/polyethelyneglycol in a ratio of 80/20 (PCL/PEG; mass/mass). 100 mg of chloramphenicol was slightly compressed under 300 mbar for half a minute to form a tablet from which small portions of approximately 12 mg were obtained. Each of these small tablets were then covered with melted copolymer to form the final ocular insert devices embodying the invention.

These ocular inserts embodying the invention in Formulation Q were of asymmetrical shape as represented in scheme B of FIG. 2. The average length of the large diameter was 8 mm while the small diameter measured 4 mm. The average weight of the ocular inserts of Formulation 10 was approximately 150 mg with approximately 12 mg of drug in a central core.

Each insert of Formulation 10 was placed in phosphate-buffered saline solution (PBS) at 37° C. until all the drug was released to the aqueous media. The chloramphenicol dissolved was quantified by an UV-Vis spectrophotometric method and the results shown a constant drug release for up 7 days, when more than 90% of chloramphenicol was already dissolved (FIG. 4Q). This release rate corresponds to an average ocular daily of approximately 1.7 mg of drug, considering the lacrimal film turnover.

EXAMPLE 11

In this example, 3 different formulations of the ocular insert embodying the invention (11, 12 and 13) are compared in terms of chloramphenicol release. The copolymer was prepared in a ratio of 80/20 (PCL/PEG; mass/mass) using a low molecular weight polycaprolactone and polyethelyneglycol with 3 distinct molecular weights—600 g/mol for formulation 11, 6,000 g/mol for formulation 12 and 35,000 g/mol for formulation 13. Chloramphenicol was mixed with the copolymer in a beaker under magnetic stirring at 70° C. for a few minutes. The drug percentage regarding the total mixture weight was 14% (mass/mass).

Ocular inserts embodying the invention were then prepared from that drug/polymer mixture with asymmetrical shape as represented in scheme B of FIG. 2. The average length of the large diameter was 5.8 mm while the small diameter measured 2.7 mm. The average weight of the ocular inserts of Formulation K was approximately 50 mg with approximately 7 mg of drug dispersed in the polymeric matrix.

Each insert of Formulation I was placed in phosphate-buffered saline solution (PBS) at 37° C. until all the drug was released to the aqueous media. The chloramphenicol dissolved was quantified by an UV-Vis spectrophotometric method and the results shown a "Fickian" release for all inserts. The release rate was dependent on the molecular weight of the PEG used in the composition—approximately 50% of the drug was released before the initial 12 hours from the insert with PEG 35000 whereas the insert with PEG 600 only released 50% of the drug after 36 hours (FIG. 4R).

These examples clearly illustrate the versatility and novelty of the invention concerning the drug release profiles that may be achieved and adapted, by changing the composition, shape and architecture of the ocular insert embodying the invention.

For manufacturers such as pharmaceutical companies, shifting from eye drops to CDDS has economic benefits, such as the product life-cycle extension, and represents a marketing opportunity based on product differentiation and innovative technology. Moreover, the amount of drug (the most expensive raw material for any dosage form) is reduced when compared to eye drops, with direct impact on the production costs.

Industrial batches of this invention can de produced by well-established manufacturing processes such as tableting by compression, including the multi-layer technology, hot-melt extrusion which improves the homogeneity of the drug distribution in the polymeric matrix and molding. Additionally 3D printing can also be applied for an even more detailed customization of the ocular insert embodying the invention.

The invention claimed is:

1. An ocular insert configured for noninvasive insertion into the upper or lower fornix conjunctiva of the eye,
   the ocular insert configured to be maintained stably in the upper or lower fornix conjunctiva of the eye for a sustained period of time and configured to deliver drugs from beneath the insert, the insert comprising:
   a drug delivery component which in turn comprises at least one polymeric layer surrounding a drug core, and
   the ocular insert having a hemispherical shape and configured to be inserted in a friction fit in the upper or lower fornix conjunctiva of the eye,
   the drug core and the polymer layer surrounding it each have the respective shape of the ocular insert,
   the drug core comprises at least a first drug and the at least one polymeric layer comprises at least a second drug, wherein the complete release of the at least first and second drugs occur by different rates, wherein such rates are linear or Fickian and allows a sustained release of the at least one first drug and at least one second drug for up to 300 days of release time, wherein the drug core is formed as a mini tablet, through the compression of the first drug either alone or with a small amount of polymer or aggregator, thereby providing a first delivery rate of the at least one first drug, such first delivery rate being linear or Fickian, and the at least one polymer layer is formed by covering the drug core with a mixture of melted polymer and the at least one second drug, such mixture being adjusted, as well as the amount of drug and of polymer, the polymer composition and the proportion drug/polymer, such that a second delivery rate of the at least one second drug is provided for each of the at least one polymer layer, such second delivery rate being linear if the first delivery rate is Fickian or Fickian if the first delivery rate is linear.

2. The ocular insert according to claim 1, wherein the at least one polymeric layer comprises a polyester, the polyester comprising one or more of polycaprolactone, poly(lactic acid), poly(glycolic acid) or their copolymers, and a polyol, the polyol comprising one or more of polyethylene glycol, castor oil or poly(vinyl alcohol), the polyol content in the final mixture of from 0% to 50%.

3. The ocular insert according to claim 2 characterized in that the polymeric composition comprises polycaprolactone (PCL) and polyethylene glycol (PEG) or copolymers thereof, the molecular weight of PCL between 500 and 30,000 g/mol and the molecular weight of PEG between 200 and 40,000 g/mol.

4. The ocular insert according to claim 3 characterized in that the polymeric composition comprises a copolymer of PCL-PEG in which the content of PEG between 10% and 30%.

5. The ocular insert according to claim 1 wherein the at least one polymeric layer further contains crosslinkers, the crosslinkers comprising one or more of acrylates or cyanates, and plasticizers, the plasticizers comprising one or more of adipates, phthalates, polymers or solvents.

6. The ocular insert according to claim 1, wherein the at least one first or second drug is released during 7 to 200 days at a linear or "Fickian" diffusion rate.

7. The ocular insert according to claim 1, wherein the insert has a symmetrical hemispherical shape with a radius between 2 and 8 mm.

8. The ocular insert according to claim 1, wherein the insert is a dome-shaped hemisphere with a diameter of 2.0 mm and a height of 0.5 mm.

9. The ocular insert according to claim 1, wherein the drug release mechanism is diffusion, osmosis, bioerosion or any combination thereof.

10. The ocular insert according to claim 1, wherein the at least one drug is chosen from antibiotics, tetracycline, chlortetracycline, bacitracin, neomycin, polymyxin, gramicidin, cephalexin, oxytetracycline, chloramphenicol kanamycin, rifampicin, gentamycin, erythromycin, penicillin, fluoroquinolone, antibacterials, sulfonamides, sulfadiazine, sulfacetamide, sulfamethiazole, sulfisoxazole, nitrofurazone, sodium propionate, antivirals, idoxuridine, trifluorothymidine, acyclovir, ganciclovir, interferon, anti-allergenics, sodium cromoglycate, antazoline, methapyrilene, chlorpheniramine, cetirizine, prophenpyridadine, anti-inflammatories, hydrocortisone, hydrocortisone acetate, dexamethasone, dexamethasone 21-phosphate, fluocinolone, medrysone, prednisolone acetate, fluoromethalone, betamethasone, triamcinolone, flurbiprofen, non-steroidal anti-inflammatory drugs, decongestants, phenylephrine, naphazoline, tetrahydrozoline, miotics, anticholinesterase drugs, pilocarpine, acetylcholine chloride, physostigmine, eserine, carbachol, di-isopropyl fluorophosphate, phospholine iodine, demecarium bromide, mydriatics, atropine sulfate, cyclopentolate, homatropine, scopolamine, tropicamide, eucatropine, hydroxyamphetamine, sympathomimetics, epinephrine, immunological drugs, vaccines, immune stimulants, hormonal agents, estrogens, estradiol, progestational, progesterone, insulin, calcitonin, parathyroid hormone, peptide, vasopressin, hypothalamus releasing factor, beta adrenergic blockers, timolol maleate, levobunolol HC1, betaxolol HC1, growth factors, epidermal growth factor, fibronectin, carbonic anhydrase inhibitors, dichlorphenamide, acetazolamide, methazolamide, prostaglandins, anti-prostaglandins, or mixtures thereof.

11. A process of making the ocular insert of claim 1 comprising:

I) producing a central core of at least one drug surrounded by a polymeric layer comprising:
  a—compressing the at least one drug either alone or with an amount of polymer or aggregator to form a mini tablet; and
  b—generating each layer by covering the previous layer of the insert with an amount of a mixture of melted polymer and drug; wherein the thickness of each layer is defined by the amount of the mixture and the radius of the ocular insert formed after the generation of each layer;
wherein the mixture in b) is produced by mixing the at least one drug with the melted polymer by stirring until a homogenous solid or gel-like compound is obtained; or
II) producing a monolithic polymer-based matrix wherein the at least one drug is dispersed in the matrix by molding or hot-melt extrusion; or
III) combining steps I and II.

* * * * *